| United States Patent [19] | [11] | 4,162,200 |
|---|---|---|
| Himmele et al. | [45] | Jul. 24, 1979 |

[54] PREPARATION OF PURE DIMETHYL CARBONATE

[75] Inventors: Walter Himmele, Walldorf; Karl Fischer, Worms; Gerd Kaibel, Lampertheim; Kurt Schneider, Bad Duerkheim; Rudolf Irnich, Bobenheim, all of Fed. Rep. of Germany

[73] Assignee: BASF Aktiengesellschaft, Fed. Rep. of Germany

[21] Appl. No.: 871,547

[22] Filed: Jan. 23, 1978

[30] Foreign Application Priority Data

Feb. 17, 1977 [DE] Fed. Rep. of Germany ....... 2706684

[51] Int. Cl.² .......................... B01D 3/40; C07C 69/00
[52] U.S. Cl. ........................................ 203/58; 203/60; 203/62; 203/67; 203/69; 260/463
[58] Field of Search ................................... 203/50–70; 260/463

[56] References Cited

U.S. PATENT DOCUMENTS

| 3,803,201 | 4/1974 | Gilpin et al. | 260/463 |
| 3,847,755 | 11/1974 | Chanel et al. | 203/60 |
| 3,963,586 | 6/1976 | Ginnasi et al. | 260/463 |

*Primary Examiner*—Wilbur L. Bascomb, Jr.
*Attorney, Agent, or Firm*—Keil & Witherspoon

[57] ABSTRACT

Dimethyl carbonate is obtained pure, from its solutions in methanol, by extractive distillation carried out with a temperature of from 60° C. at the top to 250° C. at the bottom of the column and employing, as the extractant, an aprotic organic liquid which is substantially inert toward dimethyl carbonate, boils at above 100° C. at standard pressure, is miscible with dimethyl carbonate in all proportions and has a dielectric constant $\epsilon$ of from 4 to 90 and a dipole moment $\mu$ of from 1.5 to 5 Debye.

5 Claims, No Drawings

PREPARATION OF PURE DIMETHYL CARBONATE

The present invention relates to a novel process for obtaining pure dimethyl carbonate from its solutions in methanol.

Conventionally (cf., for example, U.S. Pat. No. 3,803,201), dimethyl carbonate is prepared by transesterifying ethylene carbonate with methanol:

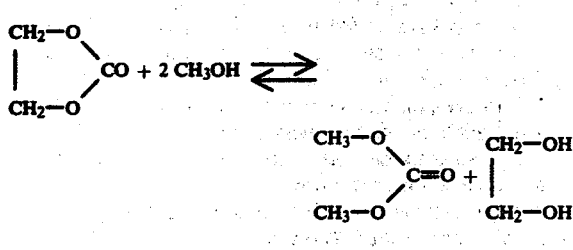

Since this is an equilibrium reaction, the dimethyl carbonate must be distilled continuously from the reaction mixture. This, however, has the disadvantage that dimethyl carbonate and methanol form an azeotrope so that, depending on the prevailing pressure, up to 30 percent strength by weight methanolic solutions of the desired product are obtained. The above Patent discloses that dimethyl carbonate can be obtained pure by crystallizing it from these solutions at about $-70°$ C.; this is an expensive method which is virtually unusable industrially.

Distillation under a pressure of 10 bars, by the method described in German Laid-Open Application DOS 2,607,003, is not a satisfactory solution of the separation problem either since it requires substantial expenditure on apparatus and energy consumption, and merely shifts the azeotrope in the direction of dimethyl carbonate.

Finally, German Laid-Open Application DOS No. 2,450,856 discloses subjecting mixtures of methanol, water and dimethyl carbonate to extractive distillation with water. Apart from the resulting danger of hydrolysis, this process is also disadvantageous because the excess methanol present passes into the aqueous phase and can only be removed therefrom at the expense of substantial heat consumption.

It is an object of the present invention to obtain dimethyl carbonate more economically from its solutions in methanol than is possible by the prior art.

We have found that this object is achieved and that dimethyl carbonate is successfully obtained in a pure form from its methanolic solutions by extractive distillation, if the extractive distillation is carried out over the temperature range of from at least 60° C. at the column top to not more than 250° C. at the column bottom and if the extractant used is an aprotic organic liquid which is substantially inert toward dimethyl carbonate, boils at above 100° C. at standard pressure, is miscible with dimethyl carbonate in all proportions and has a dielectric constant $\epsilon$ of from 4 to 90 and a dipole moment $\mu$ of from 1.5 to 5 Debye.

Further, we have found that compounds having one or more ester structures (—CO—O—) in the molecule are particularly suitable for this purpose.

The proviso that the extractant must be substantially inert toward dimethyl carbonate means that any chemical interaction under the extraction conditions only occurs to a negligible extent. Extractants which have ester groups, e.g. butanediol diacetate, can, it is true, undergo transesterification reactions with dimethyl carbonate, but virtually do not do so under the conditions of the process according to the invention.

In general, compounds from numerous chemical classes may be used as extractants, for example aromatic compounds, e.g. chlorobenzene, diethylbenzenes and benzonitrile, ketones, e.g. cyclohexanone and acetophenone, tetramethylenesulfone and amines, e.g. N,N-dimethylaniline. However, the use of some of these compounds requires additional technological measures, either because of relatively high flammability (diethylbenzene) or because of toxicity (chlorobenzene) or because of a tendency to form peroxides (cyclohexanone). Furthermore, very expensive extractants will only be used in special cases.

The process is simplest in every respect if the compounds having an ester structure, as defined above, are used. Specific examples are above all butanediol diacetate and, very especially, methylglycol acetate and butyrolactone. A selection of suitable extractants, together with their relevant physical data, is given in the Examples.

The process can be carried out in columns of conventional construction, e.g. packed columns, perforated tray columns or bubble-tray columns. The methanol/dimethyl carbonate mixture (which is most cases is the azeotrope containing 70% by weight of methanol and 30% by weight of dimethyl carbonate) is introduced, as a liquid or vapor, into the middle part of the column whilst the liquid extractant is introduced at the top and allowed to flow in counter-current to the vapors. The number of trays required for 95% extraction varies with the nature of the extractant but is in general from 10 to 70. It is true that a low number of plates is desirable but this is not an absolute criterion of the special suitability of the extractant. Inter alia, the above aspects of safety of operation must also be taken into consideration.

In general, from 0.5 to 50 kg of the extractant are used per kg of dimethyl carbonate. The optimum amounts can be determined easily by a few preliminary experiments.

The methanol which leaves at the top is recycled to the synthesis stage. Accordingly, it does not matter if the methanol still contains up to about 20% by weight of dimethyl carbonate. The dimethyl carbonate and extractant form the bottom product which is then separated into its components by flash distillation. In other respects, all techniques of conventional extractive distillation can be used, so that further details relating thereto are superfluous.

As is known, dimethyl carbonate is an important intermediate for organic syntheses, inter alia for the manufacture of crop protection agents having a methylcarbamate structure.

EXAMPLES

Per hour, 2 kg of a mixture of 70% by weight of methanol and 30% by weight of dimethyl carbonate (azeotropic boiling point 63.5° C.) were introduced into the middle of a packed column of 100 mm diameter, having 30 theoretical plates. The temperature gradient in the column ranged from 64° C. at the top to about 170° C. at the bottom, and the reflux ratio was set to 1.5. Per hour, 10 kg of an extractant E were passed through the column in counter-current to the vapor phase. The yield of virtually methanol-free dimethyl carbonate, which had been freed from extractant by distillation, was p %.

The results of the experiments are summarized below.

| Example | Extractant E | Boiling point (°C.) | Dielectric Constant ε | Dipole moment μ (Debye) | Yield p (%) |
|---|---|---|---|---|---|
| 1 | methylglycol acetate | 145 | 8.75 | 2.13 | 98 |
| 2 | chlorobenzene | 132 | 5.6 | 1.5 | 98 |
| 3 | butyrolactone | 204 | 39 | 4.1 | 95 |
| 4 | ethylene carbonate | 238 | 90 | 4.9 | 95 |
| 5 | benzonitrile | 191 | 25 | 4.05 | 92 |
| 6 | N,N-dimethylaniline | 193 | 4.5 | 1.7 | 92 |
| 7 | tetramethylenesulfone | 287 | 43 | 4.8 | 89 |
| 8 | acetophenone | 202 | 17 | 3 | 81 |
| 9 | cyclohexanone | 156 | 18 | 3 | 80 |

What we claim is:

1. A process for obtaining pure dimethyl carbonate from its solution in methanol, which comprises subjecting the solution to extractive distillation in a column over a temperature range of from at least 60° C. at the column top to not more than 250° C. at the column bottom, employing, as the extractant, an aprotic organic liquid which is substantially inert toward dimethyl carbonate, has an atmospheric boiling point above 100° C., is miscible with dimethyl carbonate in all proportions and has a dielectric constant ε of from 4 to 90 and a dipole moment μ of from 1.5 to 5 Debye.

2. A process as claimed in claim 1, wherein a compound having one or more ester structures (—CO—O—) in the molecule is used as the extractant.

3. A process as claimed in claim 2, wherein methylglycol acetate is used as the extractant.

4. A process as claimed in claim 2, wherein butyrolactone is used as the extractant.

5. A process as claimed in claim 1, carried out in a column of from 10 to 70 trays.